United States Patent
Chaplin (10) Patent No.: US 11,950,862 B2
(45) Date of Patent: Apr. 9, 2024

(54) PULLEY ARRANGEMENT AND PULLEY GUARD FOR ARTICULATING A SURGICAL INSTRUMENT

(71) Applicant: CMR Surgical Limited, Cambridge (GB)

(72) Inventor: Ben Robert Chaplin, Cambridgeshire (GB)

(73) Assignee: CMR Surgical Limited, Cambridge (GB)

( * ) Notice: Subject to any disclaimer, the term of this patent is extended or adjusted under 35 U.S.C. 154(b) by 1114 days.

(21) Appl. No.: 16/620,336

(22) PCT Filed: Jun. 6, 2018

(86) PCT No.: PCT/GB2018/051541
§ 371 (c)(1),
(2) Date: Dec. 6, 2019

(87) PCT Pub. No.: WO2018/224824
PCT Pub. Date: Dec. 13, 2018

(65) Prior Publication Data
US 2020/0138531 A1    May 7, 2020

(30) Foreign Application Priority Data

Jun. 6, 2017   (GB) ..................... 1709014

(51) Int. Cl.
*A61B 34/30*   (2016.01)
*A61B 17/29*   (2006.01)
*A61B 34/00*   (2016.01)

(52) U.S. Cl.
CPC .............. *A61B 34/30* (2016.02); *A61B 17/29* (2013.01); *A61B 34/71* (2016.02);
(Continued)

(58) Field of Classification Search
CPC .... A61B 2017/2926; A61B 2017/2939; A61B 2034/305; A61B 2034/306
See application file for complete search history.

(56) References Cited

U.S. PATENT DOCUMENTS 6,206,903 B1 *   3/2001   Ramans ................. A61B 17/29
                                                        606/205
11,109,928 B2 *  9/2021   Schuh .................... B25J 9/1612
(Continued)

FOREIGN PATENT DOCUMENTS

CN    103293834 A    9/2013
CN    104093370 A    10/2014
(Continued)

OTHER PUBLICATIONS

Search report issued in corresponding GB Patent Application No. 1709014.3, dated Nov. 30, 2017.
(Continued)

*Primary Examiner* — Martin T Ton
(74) *Attorney, Agent, or Firm* — Renner, Otto, Boisselle & Sklar, LLP (57) ABSTRACT

A surgical robotic instrument comprising: a shaft; an end effector element; an articulation connecting the end effector element to the shaft, the articulation comprising: a first joint driveable by a first pair of driving elements, the first joint permitting the end effector element to rotate about a first axis transverse to a longitudinal axis of the shaft; a second joint driveable by a second pair of driving elements; a pulley arrangement around which the second pair of driving elements is constrained to move, the pulley arrangement comprising: a first set of pulleys rotatable about the first axis; and a second set of pulleys proximal to the first set of pulleys and comprising a first pulley rotatable about a second axis, and a second pulley rotatable about a third axis parallel to and offset from the second axis; and a clevis unit comprising two
(Continued)

arms supporting the pulleys of the pulley arrangement, and a pulley guard extending from one of the arms for guarding one of the first and second pulleys.

18 Claims, 8 Drawing Sheets

(52) U.S. Cl.
CPC ............... *A61B 2017/2903* (2013.01); *A61B 2017/2929* (2013.01); *A61B 2034/302* (2016.02); *A61B 2034/305* (2016.02)

(56) References Cited

U.S. PATENT DOCUMENTS

| | | | | |
|---|---|---|---|---|
| 2008/0046122 | A1* | 2/2008 | Manzo | A61B 90/98 |
| | | | | 700/245 |
| 2014/0350570 | A1 | 11/2014 | Lee | |
| 2015/0127045 | A1* | 5/2015 | Prestel | A61B 34/30 |
| | | | | 606/208 |
| 2015/0150635 | A1* | 6/2015 | Kilroy | B25J 17/02 |
| | | | | 606/130 |
| 2015/0209965 | A1 | 7/2015 | Low et al. | |
| 2015/0313676 | A1* | 11/2015 | Deodhar | A61B 34/30 |
| | | | | 606/130 |
| 2017/0135718 | A1 | 5/2017 | Lyons | |
| 2020/0315722 | A1* | 10/2020 | Penny | A61B 90/08 |

FOREIGN PATENT DOCUMENTS

| | | |
|---|---|---|
| CN | 105163679 A | 12/2015 |
| CN | 105914697 A | 8/2016 |
| CN | 106232187 A | 12/2016 |
| EP | 2364825 A1 | 9/2011 |
| EP | 2415418 | 2/2012 |
| EP | 2415418 A1 | 2/2012 |
| GB | 2546398 | 1/2013 |
| GB | 201620998 | 1/2017 |
| GB | 2546396 A | 7/2017 |
| JP | 2011200593 A | 10/2011 |
| JP | 2015501697 A | 1/2015 |
| JP | 2016518160 A | 6/2016 |
| KR | 100956760 B1 | 5/2010 |
| KR | 20100099817 A | 9/2010 |
| WO | 2016161449 A1 | 10/2016 |
| WO | 2017/098270 | 6/2017 |

OTHER PUBLICATIONS

International Search Report and Written Opinion issued in corresponding International Patent Application No. PCT/GB2018/051541, dated Sep. 12, 2018.
Search Report and Opinion dated Sep. 13, 2022, for copending Brazilian Patent Application No. 112019025814-0.
First Office Action dated Oct. 8, 2022, for copending Chinese Patent Application No. 201880037974.3.
Notification of Reasons for Refusal dispatched Jan. 24, 2022, for corresponding Japanese Patent Application No. 2019-567378.
First Examination Report dispatched Oct. 13, 2021, for corresponding Indian Patent Application No. 201927053502.
Notice of the Granting of a Patent Right for an Invention issued for corresponding Chinese National Stage Application No. 201880037974.3, dated Jul. 26, 2023.

* cited by examiner

PULLEY ARRANGEMENT AND PULLEY GUARD FOR ARTICULATING A SURGICAL INSTRUMENT

FIELD

This invention relates to a pulley guard and pulley arrangement for articulating a robotic surgical instrument.

BACKGROUND

Figure 1:
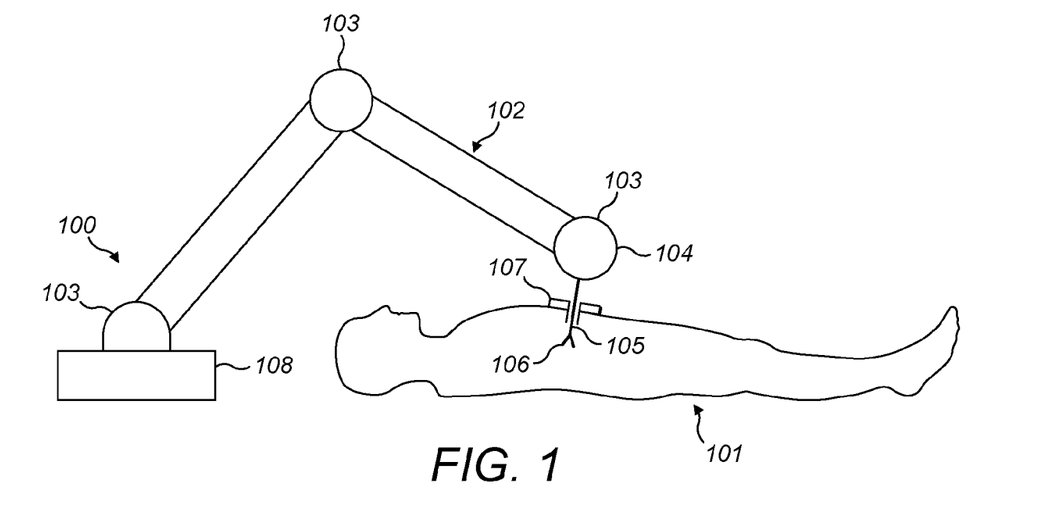
FIG. 1 illustrates a surgical robot performing a surgical procedure.

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 to access the surgical site. At its distal end, the instrument comprises an end effector 106 for engaging in a medical procedure.

Figure 2:
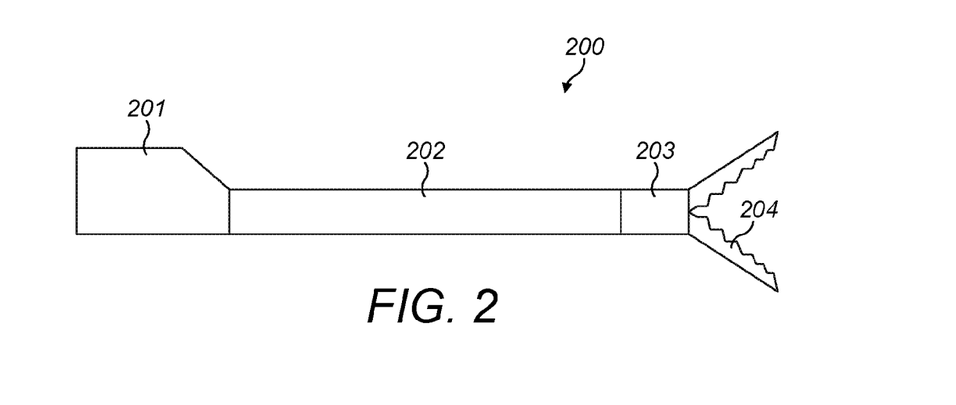
FIG. 2 illustrates a known surgical instrument.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

Figure 3:
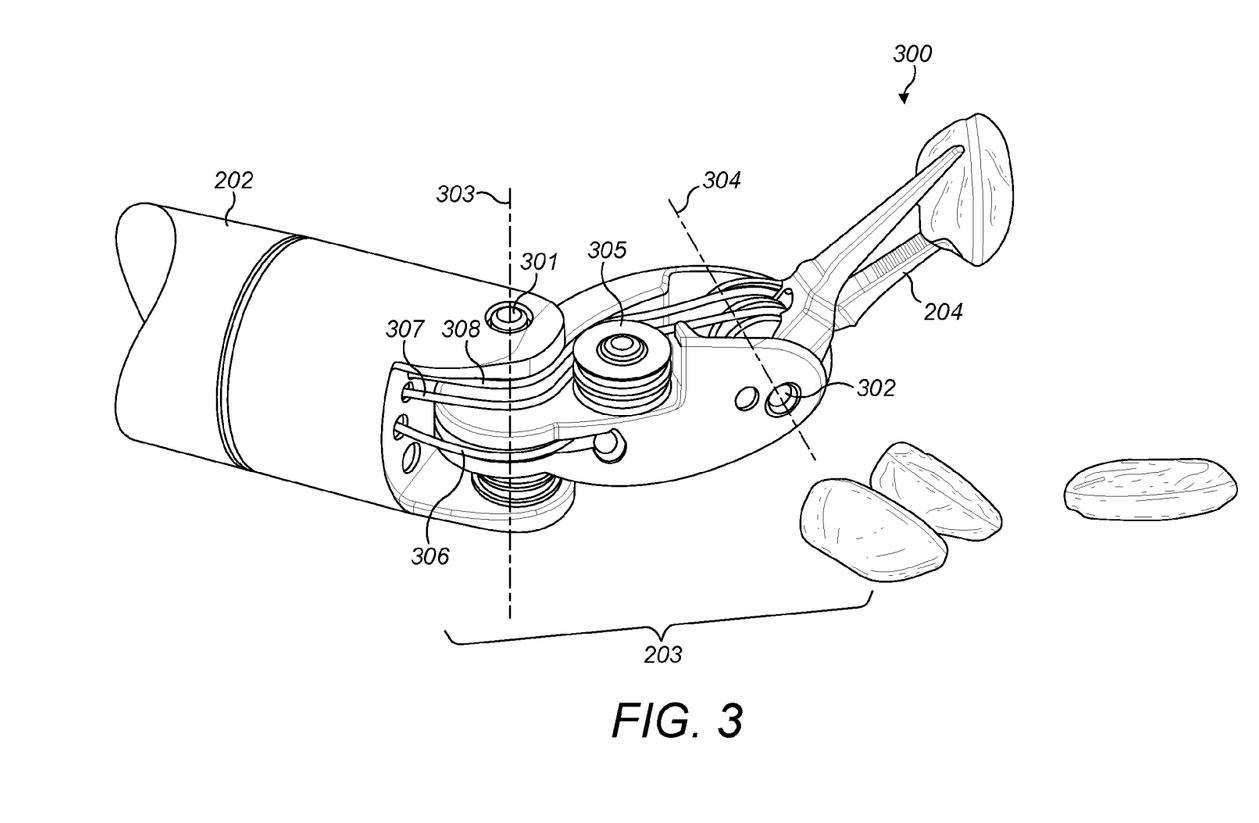
FIG. 3 illustrates a known arrangement of an articulated end effector of a surgical instrument.

FIG. 3 illustrates an example of a known surgical instrument 300 in which end effector 204 is permitted to move relative to shaft 202 by means of pitch joint 301 and two yaw joints 302. Joint 301 enables the end effector 204 to rotate about pitch axis 303. Joints 302 enable each jaw of the end effector 204 to rotate about yaw axis 304. The joints are driven by cables 306, 307 and 308. Pulley 305 is used to direct cables 307 and 308 from their passage over the pitch joint to the yaw joints. Pulley 305 is offset from the central axis of the articulation 203.

In a typical laparoscopy operation, a surgeon utilises many instruments, and hence exchanges one instrument for another many times. It is therefore desirable to minimise the time taken and maximise the ease with which one instrument is detached from a robot arm and a different instrument is attached. Additionally, it is desirable to minimise the time taken in setting up the instrument ready for use once it has been attached to the robot arm.

As such, the surgical instrument 300 may be attached at its proximal end to the distal end of the robotic arm by an instrument interface. The instrument interface may connect, or engage with, an interface of the robotic arm. Mechanical drive to drive the joints of the instrument (e.g. joints 301 and 302) may be transferred to the instrument from the robotic arm via the robotic arm interface and the instrument interface.

SUMMARY

According to the present invention there is provided a surgical robotic instrument comprising: a shaft; an end effector element; an articulation connecting the end effector element to the shaft, the articulation comprising: a first joint driveable by a first pair of driving elements, the first joint permitting the end effector element to rotate about a first axis transverse to a longitudinal axis of the shaft; a second joint driveable by a second pair of driving elements; a pulley arrangement around which the second pair of driving elements is constrained to move, the pulley arrangement comprising: a first set of pulleys rotatable about the first axis; and a second set of pulleys proximal to the first set of pulleys and comprising a first pulley rotatable about a second axis, and a second pulley rotatable about a third axis parallel to and offset from the second axis; and a clevis unit comprising two arms supporting the pulleys of the pulley arrangement, and a pulley guard extending from one of the arms for guarding one of the first and second pulleys.

The second joint may be distal to the first joint.

The second and third axes may be offset from the first axis.

The second and third axes may be offset from the first axis in a direction transverse to the longitudinal axis of the shaft.

The second and third axes may lie in a plane perpendicular to the longitudinal axis of the shaft.

The first axis may intersect the longitudinal axis of the shaft.

The second and third axes may be parallel to the first axis.

A first of the two arms may support the first pulley, and a second of the two arms may support the second pulley.

The first and second arms may be on opposing sides of a plane that contains the longitudinal axis of the shaft and is transverse to the first axis.

The clevis unit may comprise a first pulley guard extending from the first arm for guarding the first pulley, and a second pulley guard extending from the second arm for guarding the second pulley.

The first and second pulley guards may be located on opposing sides of a first plane that contains the longitudinal axis of the shaft, and is transverse to the first axis, and on opposing sides of a second plane that contains both the longitudinal axis of the shaft and the first axis.

The first pulley guard may comprise an interior sidewall that part-encompasses the first pulley, and the second pulley guard may comprise an interior sidewall that part-encompasses the second pulley.

The pulley guard(s) may be located within an interior space of the clevis unit bound by the profile of the shaft.

The clevis unit may further comprise first and second drive element guides, one driving element of the first pair of driving elements passing through the first drive element guide, and the other driving element of the first pair of driving elements passing through the second drive element guide, each of the first and second drive element guides being located between the first and second arms of the clevis unit.

The pulley guard may extend between said one of the arms and one of the drive element guides.

The first pulley guard may extend between the first arm and first drive element guide, and the second pulley guard may extend between the second arm and second drive element guide.

The first and second driving element guides may be located on opposing sides of a plane containing the longitudinal axis of the shaft and the first axis.

BRIEF DESCRIPTION OF FIGURES

The present disclosure will now be described by way of example with reference to the accompanying drawings. In the drawings.

DETAILED DESCRIPTION

Figure 4:
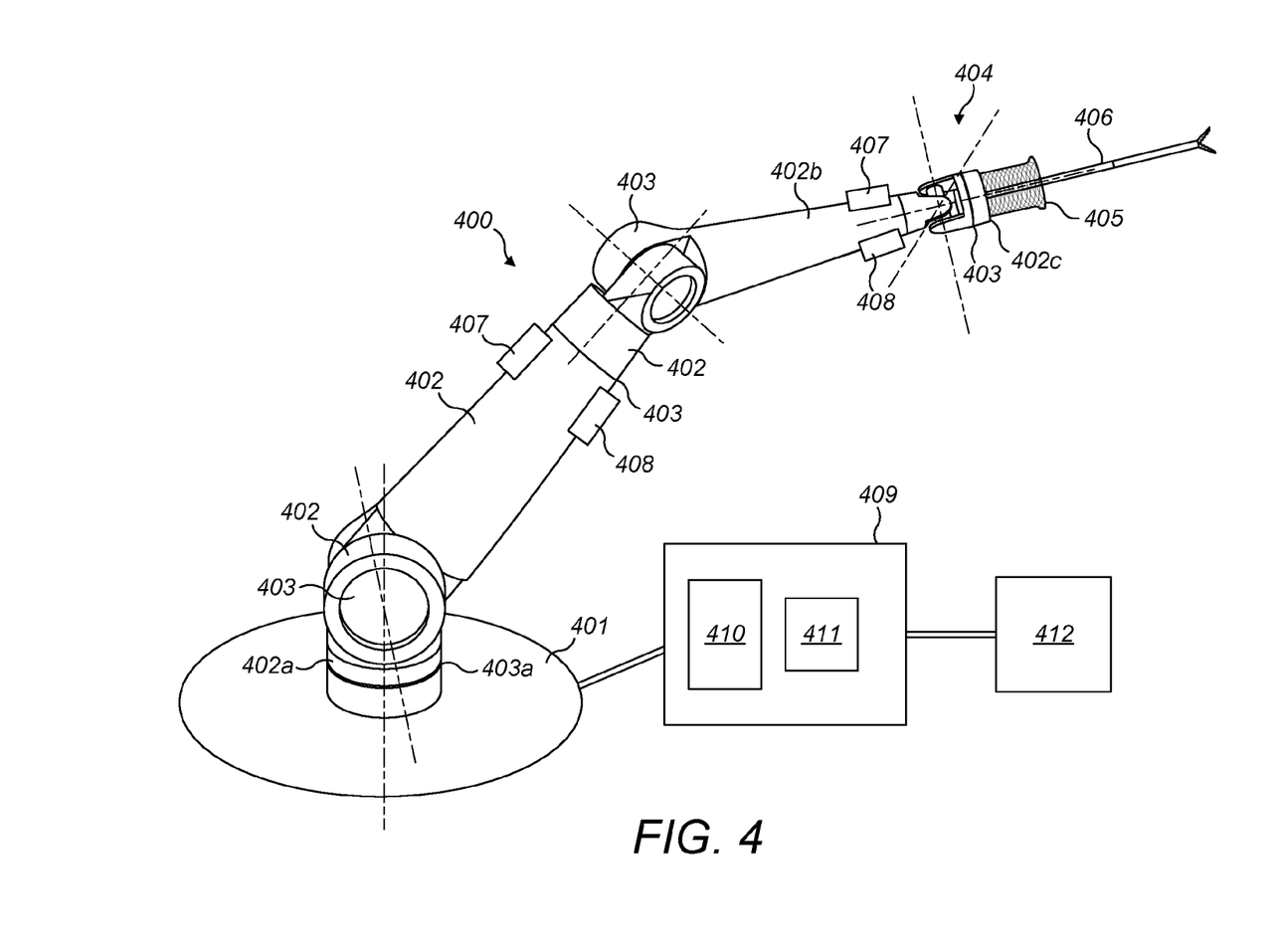
FIG. 4 illustrates a surgical robot.

FIG. 4 illustrates a surgical robot having an arm 400 which extends from a base 401. The arm comprises a number of rigid limbs 402. The limbs are coupled by revolute joints 403. The most proximal limb 402a is coupled to the base by joint 403a. It and the other limbs are coupled in series by further ones of the joints 403. A wrist 404 is made up of four individual revolute joints. The wrist 404 couples one limb (402b) to the most distal limb (402c) of the arm. The most distal limb 402c carries an attachment 405 for a surgical instrument 406. Each joint 403 of the arm has one or more motors 407 which can be operated to cause rotational motion at the respective joint, and one or more position and/or torque sensors 408 which provide information regarding the current configuration and/or load at that joint. The motors may be arranged proximally of the joints whose motion they drive, so as to improve weight distribution. For clarity, only some of the motors and sensors are shown in FIG. 4. The arm may be generally as described in our co-pending patent application PCT/GB2014/053523.

The arm terminates in an attachment 405 for interfacing with the instrument 406. The instrument 406 may take the form described with respect to FIG. 2. The attachment 405 comprises a drive assembly for driving articulation of the instrument, and a drive assembly interface for engaging an instrument interface of the instrument 406. Movable interface elements of the drive assembly interface mechanically engage corresponding movable interface elements of the instrument interface in order to transfer drive from the robot arm to the instrument. One instrument may be exchanged for another several times during a typical operation. Thus, the instrument is attachable and detachable from the robot arm during the operation. Features of the drive assembly interface and the instrument interface may aid their alignment when brought into engagement with each other, so as to reduce the accuracy with which they need to be aligned by the user.

The instrument 406 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation may comprise one or more joints which permit the end effector to move relative to the shaft of the instrument. The one or more joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 409. A control unit 409 comprises a processor 410 and a memory 411. Memory 411 stores in a non-transient way software that is executable by the processor to control the operation of the motors 407 to cause the arm 400 to operate in the manner described herein. In particular, the software can control the processor 410 to cause the motors (for example via distributed controllers) to drive in dependence on inputs from the sensors 408 and from a surgeon command interface 412. The control unit 409 is coupled to the motors 407 for driving them in accordance with outputs generated by execution of the software. The control unit 409 is coupled to the sensors 408 for receiving sensed input from the sensors, and to the command interface 412 for receiving input from it. The respective couplings may, for example, each be electrical or optical cables, or may be provided by a wireless connection. The command interface 412 comprises one or more input devices whereby a user can request motion of the end effector in a desired way. The input devices could, for example, be manually operable mechanical input devices such as control handles or joysticks, or contactless input devices such as optical gesture sensors. The software stored in memory 411 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 412 can control the instrument 406 to move in such a way as to perform a desired surgical procedure. The control unit 409 and/or the command interface 412 may be remote from the arm 400.

Figure 5A:
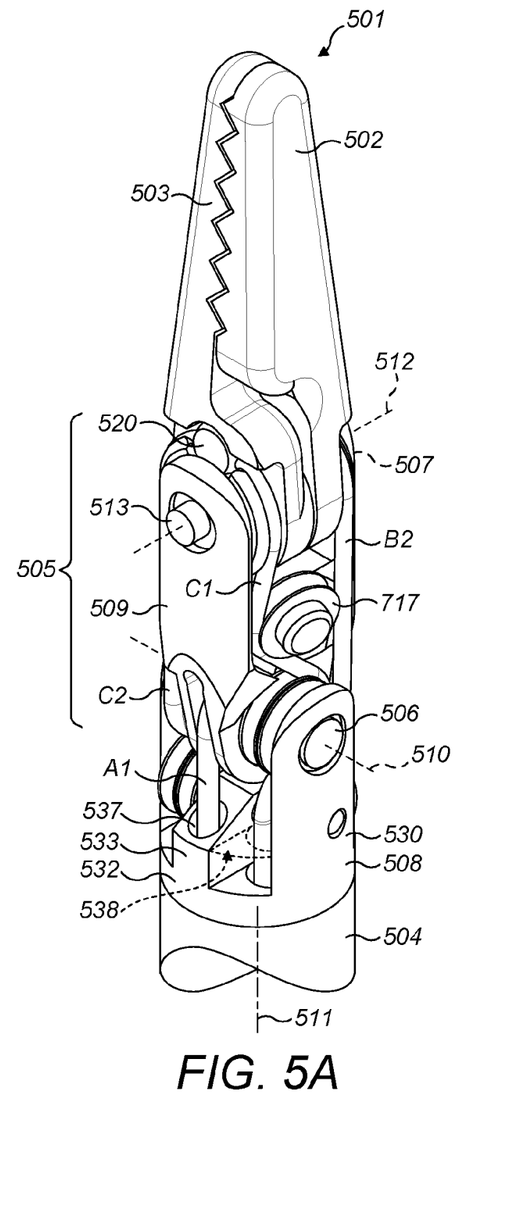
FIGS. 5a, 5b, 5c and 5d illustrate a distal end of a surgical instrument.
Figure 5B:
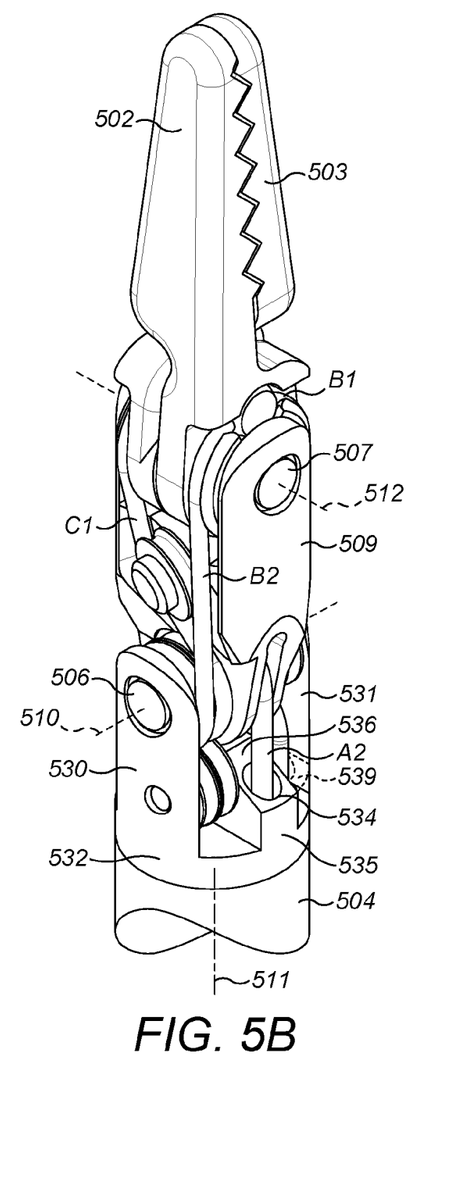

FIGS. 5a and 5b illustrate opposing views of the distal end of an example surgical instrument. In FIGS. 5a and 5b, the end effector 501 comprises a pair of end effector elements 502, 503, which in this example are depicted as a pair of opposing serrated jaws. It will be understood that this is for illustrative purposes only. The end effector may take any suitable form, such as those described above. The end effector 501 is connected to the instrument shaft 504 by articulation 505. Articulation 505 comprises joints which permit the end effector 501 to move relative to the shaft 504. In this example, the articulation 505 comprises three joints. A first joint 506 permits the end effector 501 to rotate about a first axis 510. The first axis 510 is transverse to the longitudinal axis of the shaft 511. The first joint 506 is arranged so that the shaft 504 terminates at its distal end in the joint 506. A second joint 507 permits the first end effector element 502 to rotate about a second axis 512. The second axis 512 is transverse to the first axis 510. A third joint 513 permits the second end effector element 503 to rotate about the second axis 512.

The first end effector element 502 and the second end effector element 503 may be independently rotatable about the second axis 512 by the second and third joints. The end effector elements may be rotated in the same direction or different directions by the second and third joints. The first end effector element 502 may be rotated about the second axis, whilst the second end effector element 503 is not rotated about the second axis. The second end effector element 503 may be rotated about the second axis, whilst the first end effector element 502 is not rotated about the second axis.

In the figures, the second joint 507 and third joint 513 both permit rotation about the same axis 512. However, the second and third joints may alternatively permit rotation of the end effector elements about different axes. The axis of rotation of one of the end effector elements may be offset in the longitudinal direction of the shaft 504 from the axis of rotation of the other end effector element. The axis of rotation of one of the end effector elements may be offset in a direction transverse to the longitudinal direction of the shaft 504 from the axis of rotation of the other end effector element. The axis of rotation of one of the end effector elements may not be parallel to the axis of rotation of the other end effector element. The axes of rotation of the end effector elements 502, 503 may be offset in the longitudinal direction of the shaft and/or offset in a direction perpendicular to the longitudinal direction of the shaft and/or angled with respect to each other. This may be desirable as a result of the end effector elements being asymmetric. For example, in an electrosurgical element, a first end effector element may be powered and a second end effector element not powered and insulated from the first end effector element. To aid this, the axes of rotation of the two end effector elements may be offset in the direction perpendicular to the longitudinal direction of the shaft. In another example, a first end effector element may be a blade and a second end effector element a flat cutting surface. To aid use of the blade, the axes of rotation of the two end effector elements may be angled to one another.

FIGS. 5a and 5b depict a straight configuration of the surgical instrument in which the end effector is aligned with the shaft 504. In this orientation, the longitudinal axis of the shaft 511 is coincident with the longitudinal axis of the articulation and the longitudinal axis of the end effector. Articulation of the first, second and third joints enables the end effector to take a range of attitudes relative to the shaft.

The articulation 505 comprises a supporting body 509. At one end, the supporting body 509 is connected to the shaft 504 by the first joint 506. At its other end, the supporting body 509 is connected to the end effector 501 by second joint 507 and third joint 513. Thus, first joint 506 permits the supporting body 509 to rotate relative to the shaft 504 about the first axis 510; and the second joint 507 and third joint 513 permit the end effector elements 502, 503 to rotate relative to the supporting body 509 about the second axis 512. The supporting body 509 supports the joints 507 and 513, and may also be referred to as a yoke. In the straight configuration shown in FIG. 5, the joints 507 and 513 are distal of the joint 506 in the direction of the longitudinal axis of the shaft 511 (i.e., the joint 506 is proximal of the joints 507 and 513 in the direction of the longitudinal axis of the shaft 511). It will be appreciated that the joints 507 and 513 will be distal of the joint 506 in other configurations of the surgical instrument.

The instrument further comprises a clevis unit 508. The clevis unit is located at the distal end of the shaft 504. The shaft may terminate at the clevis unit. The clevis unit is proximal of the supporting body 509 in the direction of the longitudinal axis 511 when the instrument is in the straight configuration shown in FIG. 5 (i.e., the supporting body is distal of the clevis unit). It will be appreciated that there exist other configurations of the instrument in which the clevis unit is proximal of the supporting body. The clevis unit comprises a base portion 532. The base portion is at the proximal end of the clevis unit. The base portion 532 comprises an outer wall, or surface, defining a circumference of the clevis unit. The outer surface of the base portion is flush with the outer surface of the distal end of the shaft 504. The clevis unit further comprises a pair of opposing arms 530 and 531 that support the first joint 506. The arms extend from the base portion 532. The arms extend in a direction parallel to the longitudinal axis of the shaft 511. The arms extend towards the distal end of the instrument. The arms 530 and 531 are located on opposite sides of a plane that contains the longitudinal axis of the shaft 511 and is transverse to the rotation axis 510 of the first joint 506. The arms may be evenly spaced around the circumference of the clevis unit 508. That is, the arms may be spaced apart in the direction of the rotation axis 510. The arms may also be referred to herein as tines.

The clevis unit further comprises driving element guides 533 and 534. The driving elements will be described below. Each guide 533,534 is in the form of a block that protrudes from the base portion 532 of the clevis unit. The block protrudes towards the distal end of the instrument in the straight configuration shown in FIG. 5. Equivalently, the block can be said to protrude distally in a direction parallel to the longitudinal axis of the shaft 511. Each driving element guide comprises an outer surface, or sidewall (shown at 535 for guide 534). The outer wall is flush with the outer surface of the base portion 532. The driving element guides further comprise an upper surface (shown for guide 534 at 536). In the examples shown, the upper surface of the driving element guide is a chamfer. Each driving element guide further comprises a bore, shown at 537 for guide 533. The bore extends through the guide in a direction parallel to the longitudinal axis of the shaft 511. The driving element guides are located on opposite sides of a plane that contains both the longitudinal axis of the shaft 511 and the first rotation axis 510 of the joint 506. Each driving element guide is located between the two tines 530 and 531. The guides may be equally spaced around the circumference of the base portion (as shown in the figures). Thus, in the figures, the guides are spaced apart in the direction parallel to the rotation axis 512 of the joints 507 and 513. In some examples, the driving element guides 533, 534 may be separate and distinct blocks. In other examples, the driving element guides 533, 534 may be portions of the same block. In other words, in some examples, the driving element guides 533, 534 may be combined to form a single block.

Figure 5C:
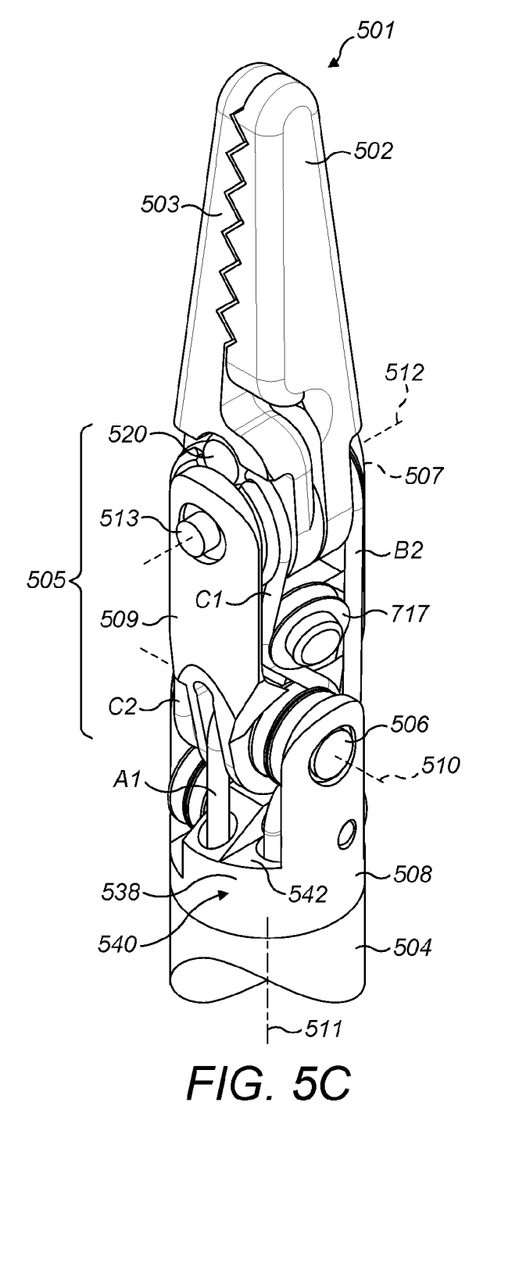
Figure 5D:
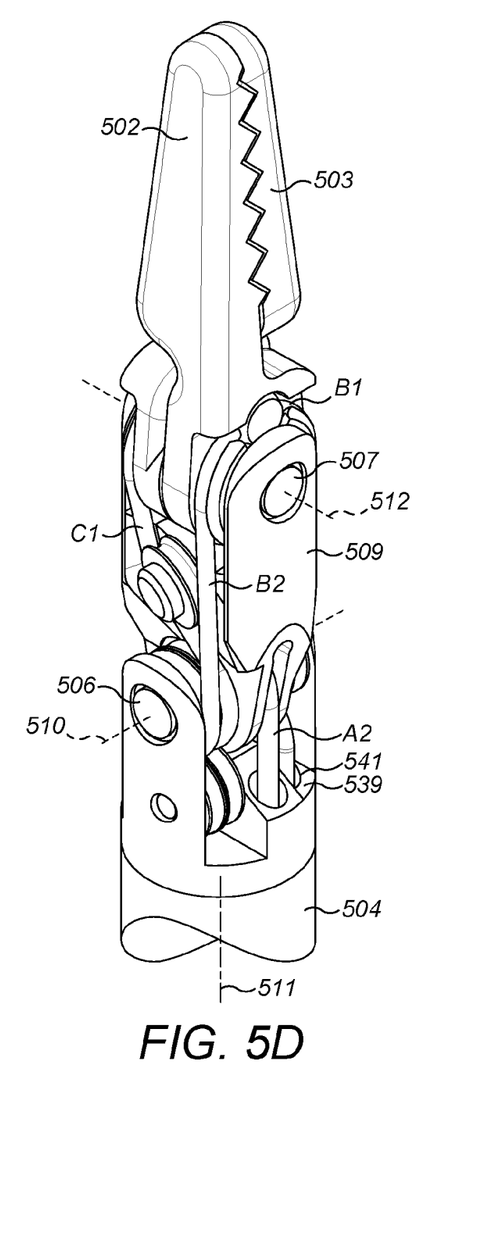

The clevis unit additionally comprises pulley guards 538 and 539. The pulley guards are delineated in FIGS. 5a and 5b by dashed lines. This is in order to show the elements of the instrument that would otherwise be obscured from view by the pulley guards. FIGS. 5c and 5d show the same views of the surgical instrument as FIGS. 5a and 5b, but with the pulley guards shown in solid form. Each pulley guard extends from a respective tine. Specifically, pulley guard 538 extends from tine 530, and pulley guard 539 extends from tine 531. The pulley guards may be said to abut the tines. In such an arrangement, the pulley guards may conveniently operate to increase the stiffness of the tines. Each pulley guard extends from a single side (that is, edge) of the tine. That is, each pulley guard abuts a single side, or edge, of the tine. In the example shown, each pulley guard extends between a tine and a driving element guide. Specifically, pulley guard 538 extends between tine 530 and driving element guide 533, and pulley guard 539 extends between tine 531 and driving element guide 534. Suitably, each pulley guard abuts a driving element guide.

The pulley guards also extend distally from the base portion 532 of the clevis unit. In the examples shown, the pulley guards protrude from the base portion to a position level with the lower edge of the chamfer 536 (that is, the edge between the chamfer and the sidewall 535 of the driving element guide). However, it will be appreciated that in other examples, the pulley guard may protrude to a greater or lesser extent. The pulley guard comprises an outer sidewall (shown at 540 for the pulley guard 538 in FIG. 5c) that is flush with the outer sidewalls of the driving element guide and the tine. It can be seen that the pulley guards occupy an interior space of the clevis unit between the driving element guide and the tine. That is, the pulley guard occupies an interior space that is bounded by the projected profile of the clevis unit 508 and shaft 504. Because the pulley guards in this example extend between the tines and driving element guides, they may be referred to herein as fillets.

The pulley guards 538 and 539 are located on opposite sides of a plane containing the longitudinal axis of the shaft 511 and the rotation axis 510 of the first joint 506. The pulley guards are also located on opposite sides of a plane containing axis 511 that is transverse to the rotation axis 510 of the first joint 506. The pulley guards may therefore be said to be diagonally opposed. Alternatively, the pulley guards may be said to be diagonally orientated with respect to the tines 530 and 531. That is, the pulley guards may lie on an axis that is diagonal to an axis on which tines 530 and 531 lie.

The pulley guards may be a separate component that is secured, or attached, to the tines. Alternatively, the pulley guards may be integrally formed with the tines (and in the examples shown, the driving element guides).

The joints of the articulation 505 are driven by driving elements. The driving elements are elongate elements which extend from the joints in the articulation through the shaft 504 to the instrument interface. Each driving element may be capable of being flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements may be inflexible along their main extents. The driving elements may resist compression and tension forces applied along their length. In other words, the driving elements may resist compression and tension forces acting in the direction of their longitudinal axes. The driving elements may have a high modulus. The driving elements may remain taut in operation; they may be not permitted to become slack. Thus, the driving elements are able to transfer drive from the instrument interface to the joints. The driving elements may be cables, for example.

Each joint may be driven by a pair of driving elements. Referring to FIGS. 5a and 5b, the first joint 506 is driven by a first pair of driving elements A1,A2. It can be seen that driving elements A1,A2 extend through the bore of driving element guides 533,534 respectively. The driving element guides therefore encompass the driving elements A1,A2 along a portion of their length. The driving element guides therefore retain the driving element A1,A2 and shield the driving elements from interference within the distal region of the end effector 501. The second joint 507 is driven by a second pair of driving elements B1,B2. The third joint is driven by a third pair of driving elements C1,C2. Each joint of the articulation 505 is therefore driven by its own pair of driving elements. In other words, each joint is driven by a dedicated pair of driving elements. The joints may be independently driven. A pair of driving elements may be constructed as a single piece as shown for the third pair of driving elements in FIGS. 5a and 5b. In this case, the single piece is secured to the joint at one point. For example, the third pair of driving elements C1,C2 comprises a ball feature 520 which is secured to the third joint 513. This ensures that when the pair of driving elements is driven, the drive is transferred to motion of the joint about its axis. Alternatively, a pair of driving elements may be constructed as two pieces. In this case, each separate piece is secured to the joint. The first, second and third pairs of driving elements extend through the instrument shaft from the distal end of the shaft connected to the articulation to the proximal end of the shaft connected to a drive mechanism of the instrument interface.

The surgical instrument of FIGS. 5a and 5b further comprises a pulley arrangement around which the second and third pairs of driving elements are constrained to move. The pulley arrangement is better illustrated in FIGS. 6a and 6b. The supporting body 509 is not shown in FIGS. 6a and 6b in order to more clearly illustrate the pulley arrangement. The pulley guards 538 and 539 are also not shown in FIGS. 6a and 6b to more clearly illustrate the pulley arrangement. The pulley arrangement comprises a first set of pulleys 601. The first set of pulleys 601 is rotatable about the first axis 510. Thus, the first set of pulleys 601 rotate about the same axis as the first joint 506. The pulley arrangement further comprises a second set of pulleys 602. The pulley arrangement further comprises a pair of redirecting pulleys 603, which are described in more detail following the description of the pulley arrangement.

Figure 7:
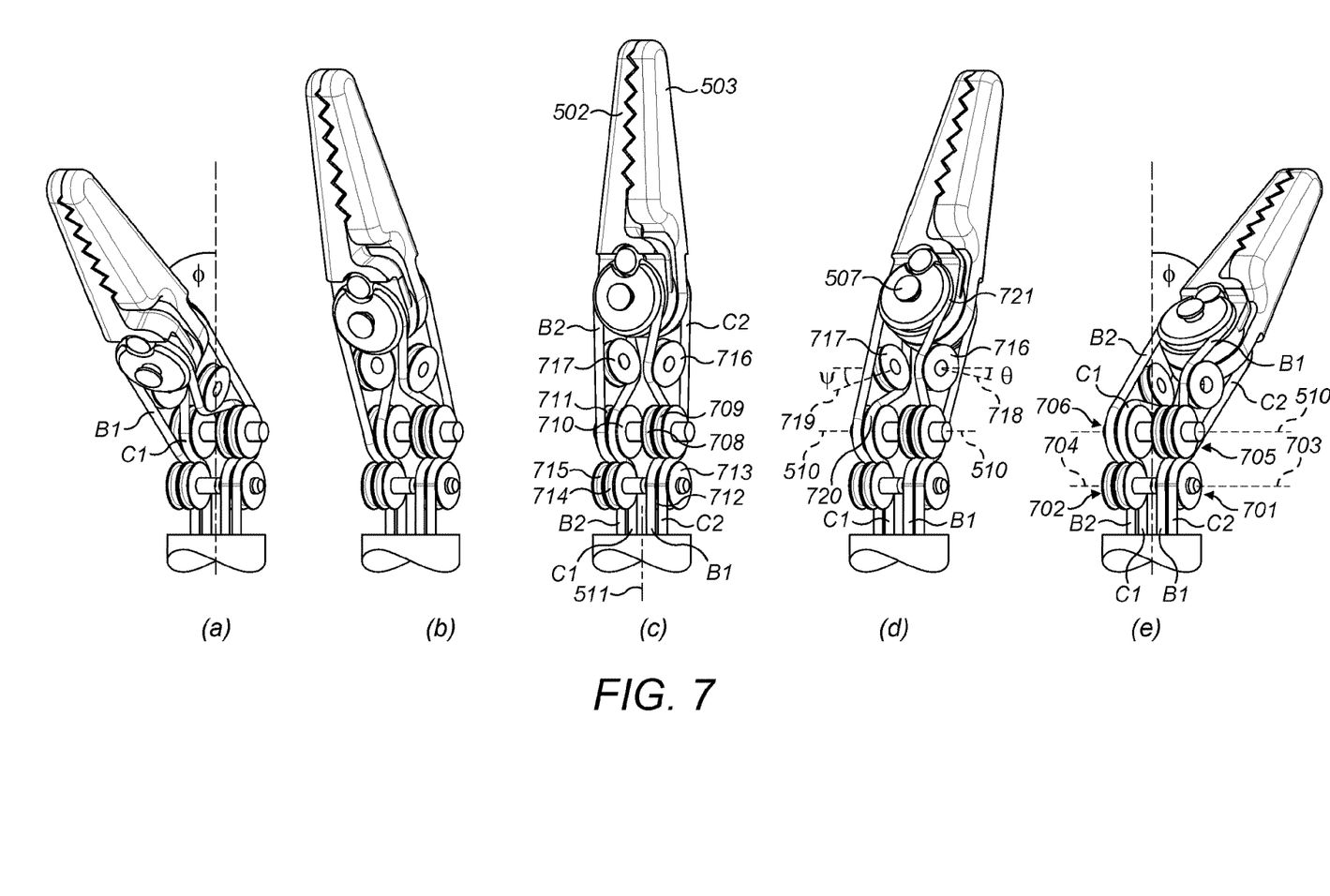
FIG. 7 illustrates a pulley arrangement of the distal end of the surgical instrument of FIGS. 5a to 5d in a variety of non-straight configurations.

The pulley arrangement is also illustrated in FIG. 7. The supporting body, the clevis unit, the first joint and the first pair of driving elements have all been omitted from FIG. 7 in order to more clearly illustrate the pulley arrangement.

The first set of pulleys 601 comprises a first pulley 705 and a second pulley 706. Both the first pulley 705 and the second pulley 706 rotate about the first axis 510. The first pulley 705 and the second pulley 706 of the first set of pulleys are located on opposing sides of the first joint 506 in a longitudinal direction of the shaft 504. The first pulley 705 and the second pulley 06 are located on opposing ends of the first axis 510. The first pulley 705 and the second pulley 706 are located on opposing sides of the first pair of driving elements A1,A2. The first set of pulleys 601 are supported by the arms 530 and 531 of the clevis unit 508. Both the first pulley 705 and the second pulley 706 of the first set of pulleys are rotatably mounted to the clevis unit. Pulley 705 is mounted to the arm 531 and pulley 706 is mounted to the arm 530.

Figure 6A:
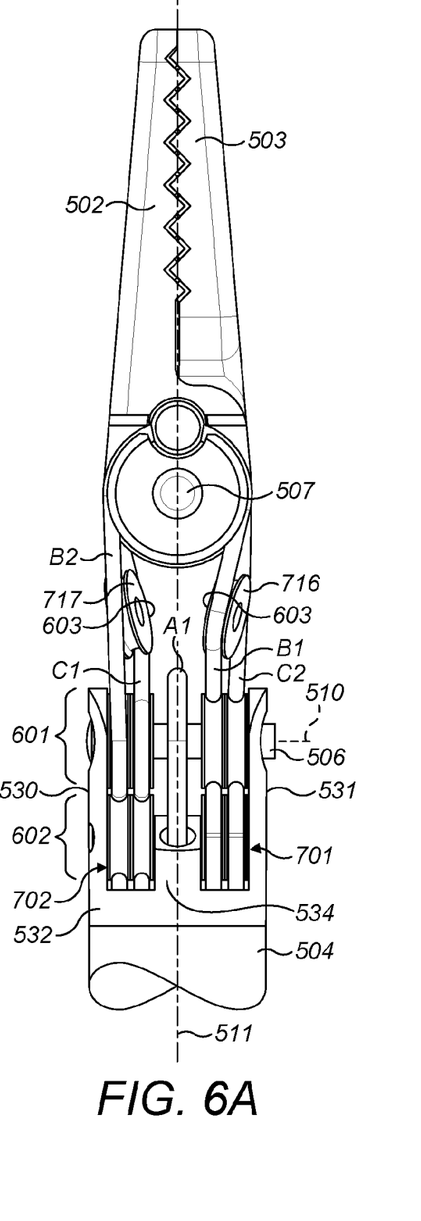
FIGS. 6a and 6b illustrate a pulley arrangement of the distal end of the surgical instrument of FIGS. 5a to 5d in a straight configuration.
Figure 8:
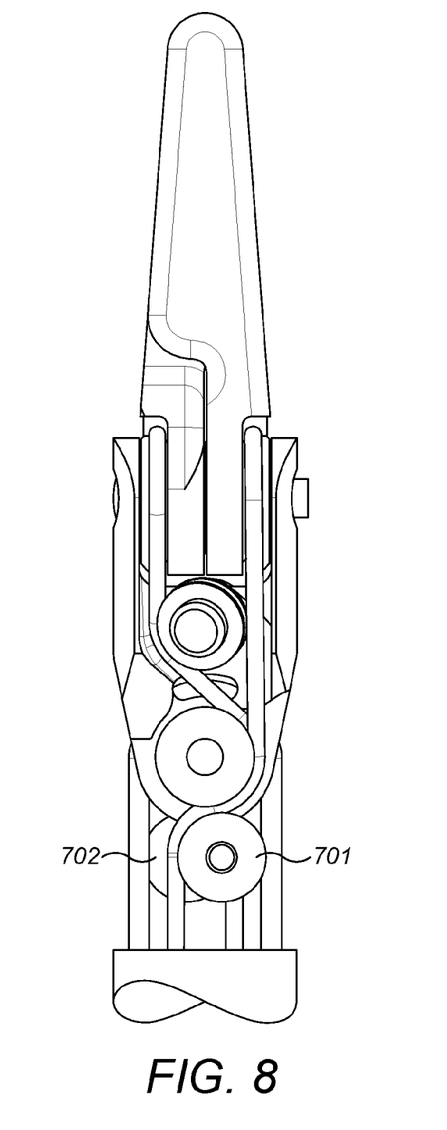
FIG. 8 illustrates the offset pulleys of the pulley arrangement shown in FIGS. 5a to 5d.

The second set of pulleys comprises a first pulley 701 and a second pulley 702. The second set of pulleys are also supported by the arms 530 and 531 of the clevis unit 508. Both the first pulley 701 and the second pulley 702 of the second set of pulleys are rotatably mounted to the clevis unit. Pulley 701 is mounted to the arm 531 and pulley 702 is mounted to the arm 530. Thus, each arm of the clevis unit supports one pulley of the second set of pulleys. The second set of pulleys 701 and 702 are additionally supported by the driving element guides 533 and 534. The first pulley 701 is supported by the driving element guide 533, and the second pulley 702 is supported by the driving element guide 534. Each driving element guide therefore supports one pulley of the second set of pulleys. Pulley 701 is therefore supported by arm 531 and driving element guide 533; and pulley 702 is supported by arm 530 and driving element guide 534. The pulleys 701 and 702 may be mounted to spindles secured to the arms 530,531 and driving element guides 533 and 534. The first pulley 701 is rotatable about a third axis 703 which is parallel to the first axis 510. The third axis 703 is offset from the first axis 510 both in the longitudinal direction of the shaft and also transverse to the longitudinal direction of the shaft. The second pulley 702 is rotatable about a fourth axis 704 which is parallel to the first axis 510. The fourth axis 704 is offset from the first axis 510 both in the longitudinal direction of the shaft and also transverse to the longitudinal direction of the shaft. The third and fourth axes are parallel but offset from each other. The third and fourth axes are offset from each other in the direction of the rotation axis 512 of the joints 507 and 513. The third axis 703 and fourth axis 704 are in the same plane perpendicular to the longitudinal direction of the shaft 511. FIG. 8 illustrates the distal end of the surgical instrument from a different view which more clearly shows the offset axes of the first pulley 701 and the second pulley 702 of the second set of pulleys. By offsetting the first pulley 701 and the second pulley 702, the driving element wrapped around each pulley is able to extend down the shaft after having wrapped around the pulley. As shown in FIG. 6a, the first pulley 701 and second pulley 702 of the second set of pulleys 602 are located on opposing sides of the first joint 506 in a longitudinal direction of the shaft 504. The first pulley 701 and second pulley 702 are located on opposing sides of the first pair of driving elements A1,A2. The offset of the pulleys 702 and 701 in the direction perpendicular to both the longitudinal axis of the shaft 511 and the rotation axis 510 of the joint 506 provides the space to accommodate the pulley guards 538 and 539.

Figure 6B:
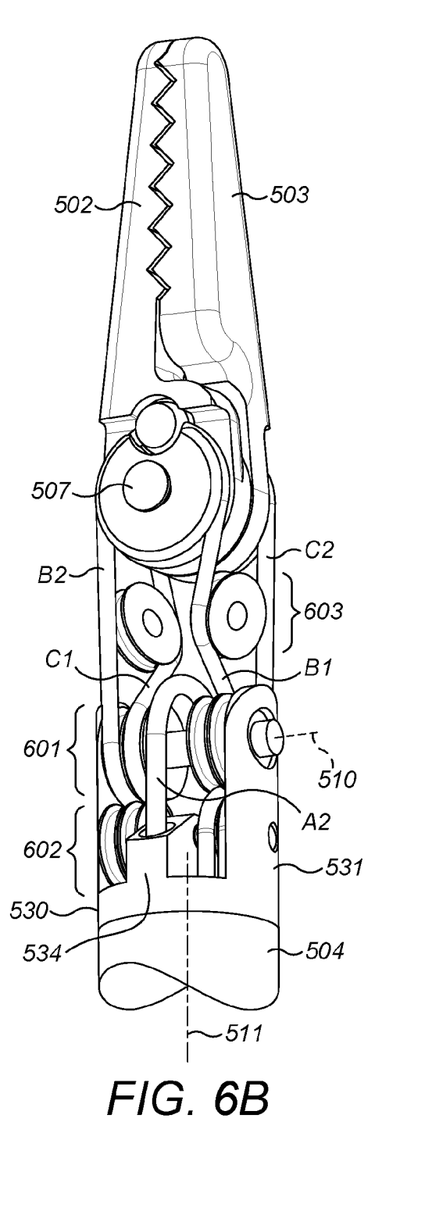

The second set of pulleys is located between the first set of pulleys and the instrument interface end of the shaft. Suitably, the second set of pulleys is located within the shaft as shown in the figures. Thus, the second set of pulleys 602 is proximal of the first set of pulleys 601 along the direction of the longitudinal axis of the shaft 511 (i.e., the first set of pulleys 601 is distal of the second set of pulleys 602). Because both sets of pulleys are supported by the clevis unit 508, it will be understood that the second set of pulleys 602 are proximal of the first set of pulleys independently of the configuration of the instrument and end effector. By locating the second set of pulleys at the distal end of the shaft 508, the distance between the first and second joints is reduced compared to the alternative arrangement in which the second set of pulleys are located in the articulation, thereby reducing the stiffness of the supporting body 509 required to maintain accurate positioning of the end effector 501.

It was mentioned above that the pulley arrangement operates to constrain the motion of the driving elements. In more detail, the second pair of driving elements B1,B2 is constrained to move around opposing sides of the first pulley 705 and the second pulley 706 of the first set of pulleys 601. The second pair of driving elements B1,B2 is constrained to move around opposing sides of the first pulley 701 and the second pulley 702 of the second set of pulleys 601. The second pair of driving elements is constrained to move around opposing sides of the first pulley 705 of the first set of pulleys 601 and the first pulley 701 of the second set of pulleys 602. The second pair of driving elements is constrained to move around opposing sides of the second pulley 706 of the first set of pulleys 601 and the second pulley 702 of the second set of pulleys 602.

The third pair of driving elements C1,C2 is constrained to move around opposing sides of the first pulley 705 and the second pulley 706 of the first set of pulleys 601. The third pair of driving elements C1,C2 is constrained to move around opposing sides of the first pulley 701 and the second pulley 702 of the second set of pulleys 601. The third pair of driving elements is constrained to move around opposing sides of the first pulley 705 of the first set of pulleys 601 and the first pulley 701 of the second set of pulleys 602. The third pair of driving elements is constrained to move around opposing sides of the second pulley 706 of the first set of pulleys 601 and the second pulley 702 of the second set of pulleys 602.

The second and third pairs of driving elements are each constrained to extend over the first joint 506 in order to reach the second and third joints respectively. Thus, the first one of the second pair of driving elements B1 passes over one side of the first pulley 705 of the first set of pulleys on the first joint axis 510, and the second one of the second pair of driving elements B2 passes over an opposing side of the second pulley 706 of the first set of pulleys on the first joint axis 510, so that whatever rotation there is of the supporting body 509 about the first joint 506, the length of the second pair of driving elements B1,B2 is maintained the same. Similarly, the first one of the third pair of driving elements C1 passes over one side of the second pulley 706 of the first set of pulleys on the first joint axis 510, and the second one of the third pair of driving elements C2 passes over an opposing side of the first pulley 705 of the first set of pulleys on the first joint axis 510, so that whatever rotation there is of the supporting body 509 about the first joint 506, the length of the third pair of driving elements C1,C2 is maintained the same. If the arrangement of the instrument interface is symmetric for both the second pair of driving elements B1,B2 and the third pair of driving elements C1,C2, then the length of the second pair of driving elements is the same as the length of the third pair of driving elements for all rotation angles of the supporting body 509 about the first joint 506. In every configuration of the surgical instrument, the second pair of driving elements and the third pair of driving elements remain taut. They are never slack. Thus, there is no backlash when articulating any of the joints of the surgical instrument. Thus, full control of all three degrees of freedom of movement of the surgical instrument is achieved in every configuration of the surgical instrument.

FIG. 7 illustrates the distal end of the surgical instrument in five different configurations. Configuration (c) is the straight configuration previously mentioned, in which the end effector is aligned with the instrument shaft. In configurations (a), (b), (d) and (e), rotation about the first joint has occurred relative to configuration (c). In configurations (a), (b), (d) and (e), no rotation about either the second or third joint has occurred relative to configuration (c). Starting from configuration (c), the driving element A2 (not shown) is pulled in order to cause the rotation about the first axis 510 leading to the arrangement of configuration (b). The driving element A2 is further pulled to cause further rotation about the first axis 510 to lead to the arrangement of configuration (a). Starting from configuration (c), the driving element A1 (not shown) is pulled in order to cause rotation about the first axis 510 in an opposing direction to that in configurations (a) and (b), thereby leading to the arrangement of configuration (d). The driving element A1 is further pulled to cause further rotation about the first axis 510 to lead to the arrangement of configuration (e).

Rotation of the end effector 501 about the first axis 510 is bounded by the maximum travel of the first pair of driving elements A1,A2 about the first joint 506. Configuration (a) shows the end effector 501 at maximum rotation about the first axis 510 in one direction, and configuration (e) shows the end effector 501 at maximum rotation about the first axis 510 in the opposing direction. The maximum rotation angle relative to the longitudinal axis of the shaft 511 in both configurations is the angle φ. The second set of pulleys 602 are located relative to the first set of pulleys 601 so as to ensure that the second and third pairs of driving elements are retained in contact with both the first set of pulleys 601 and the second set of pulleys 602 even at the maximum rotation angle φ. For all rotation angles of the end effector 501 about the first axis 510, the end effector 501 always lies within the cone defined by the tangential line connecting the first pulley 701 of the second set of pulleys and the first pulley 705 of the first set of pulleys. That tangential line is the path taken by the driving element. The end effector 501 lies in this cone when the second and third joints are retained in the straight configurations of FIGS. 5a and 5b, as shown in all the configurations of FIG. 7. As can be seen from FIG. 7, without the second set of pulleys 602, the driving elements B2 and C1 would lose contact with the first set of pulleys 601 in configuration (a). Without the second set of pulleys 602, the driving elements B1 and C2 would lose contact with the first set of pulleys 601 in configuration (e).

The second and third pairs of driving elements are retained in contact with the first and second sets of pulleys for all rotation angles of the end effector relative to the longitudinal axis of the shaft. Thus, regardless of the rotation about the first joint 506, the length of the second pair of driving elements B1,B2 will be maintained the same. Also, regardless of the rotation about the first joint 506, the length of the third pair of driving elements C1,C2 will be maintained the same. Thus, the second set of pulleys enable tension to be retained in the second and third driving elements regardless of how the first joint 506 is driven about the first axis 510. Thus, control of the second and third driving elements is retained regardless of how the first joint 506 is driven about the first axis 510.

In the examples illustrated here, each pulley of the first set of pulleys 601 comprises a pair of pulley elements. The first pulley 705 comprises an inside pulley element 708 and an outside pulley element 709. Inside pulley element 708 is located between the outside pulley element 709 and the first pair of driving elements A1,A2. Suitably, inside pulley element 708 abuts outside pulley element 709. The inside pulley element 708 may be fast with the outside pulley element 709. The inside pulley element 708 may be integrally formed with the outside pulley element 709. The second pulley 706 comprises an inside pulley element 710 and an outside pulley element 711. Inside pulley element 710 is located between the outside pulley element 711 and the first pair of driving element A1,A2. Suitably, inside pulley element 710 abuts outside pulley element 711. The inside pulley element 710 may be fast with the outside pulley element 711. The inside pulley element 710 may be integrally formed with the outside pulley element 711. Each pulley element comprises a groove for seating a driving element.

Suitably, each pulley of the second set of pulleys 602 comprises a pair of pulley elements. The first pulley 701 comprises an inside pulley element 712 and an outside pulley element 713. Inside pulley element 712 is located between the outside pulley element 713 and the first pair of driving elements A1,A2. Suitably, inside pulley element 712 abuts outside pulley element 713. The inside pulley element 712 may be fast with the outside pulley element 713. The inside pulley element 712 may be integrally formed with the outside pulley element 713. The second pulley 702 comprises an inside pulley element 714 and an outside pulley element 715. Inside pulley element 714 is located between the outside pulley element 715 and the first pair of driving element A1,A2. Suitably, inside pulley element 714 abuts outside pulley element 715. The inside pulley element 714 may be fast with the outside pulley element 715. The inside pulley element 714 may be integrally formed with the outside pulley element 715. Each pulley element comprises a groove for seating a driving element.

The second pair of driving elements B1,B2 is constrained to move around the inside pulley element 712 of the first pulley of the second set of pulleys and the outside pulley element 715 of the second pulley of the second set of pulleys. The second pair of driving elements B1,B2 is constrained to move around the inside pulley element 708 of the first pulley of the first set of pulleys and the outside pulley element 711 of the second pulley of the first set of pulleys.

The third pair of driving elements C1,C2 is constrained to move around the outside pulley element 713 of the first pulley of the second set of pulleys and the inside pulley element 714 of the second pulley of the second set of pulleys. The third pair of driving elements C1,C2 is constrained to move around the outside pulley element 709 of the first pulley of the first set of pulleys and the inside pulley element 710 of the second pulley of the first set of pulleys.

Thus, the second pair of driving elements B1,B2 has a symmetrically opposing path around the first and second sets of pulleys 601, 602 than the third pair of driving elements C1,C2. In the straight configuration of the instrument in which the end effector is aligned with the shaft, the path of the second pair of driving elements B1,B2 about the pulley arrangement is rotationally symmetrical about the longitudinal axis of the shaft 511 to the path of the third pair of driving elements C1,C2 about the pulley arrangement. The second and third pairs of driving elements B1,B2 and C1,C2 emerge from the second set of pulleys 602 into the distal end of the shaft in a symmetrical arrangement. As can be more easily seen on FIG. 7, the driving elements B1 and C2 emerge adjacent to each other on one side of the shaft, and the driving elements C1 and B2 emerge adjacent to each other on an opposing side of the shaft. The arrangement of driving elements B1 and C2 in the shaft is rotationally symmetrical to the arrangement of driving elements C1 and B2 in the shaft, about the longitudinal axis of the shaft 511. The second set of pulleys 602 redirects the second and third pairs of driving elements from the first set of pulleys 601 into the shaft in this manner.

Now that the pulley arrangement of the end effector has been explained in more detail, the role of the pulley guards can be more readily understood. It can be seen with reference to FIGS. 6 and 7 that the pulley guard 539 guards the first pulley 701 of the second set of pulleys 602. It also guards the driving elements B1 and C2 wrapped around that pulley as those elements extend into the shaft. That is, the pulley guard 539 shields the portion of the driving elements extending between the pulley 701 and the distal terminal end of the shaft. As can be seen most clearly with reference to FIG. 5d, the pulley guard 539 comprises an inner sidewall 541 (only the tope edge of which can be seen in the figure) that part-encompasses a driving element that wraps around the pulley 701. This assists in shielding the driving element.

Analogously, pulley guard 538 guards the second pulley 702 of the second set of pulleys 602. It also guards the driving elements B2 and C1 wrapped around that pulley as those elements extend into the shaft. The portion of the driving elements extending between the pulley 702 and the distal terminal end of the shaft are shielded by the pulley guard 538. As can be seen most clearly with reference to FIG. 5c, the pulley guard 538 comprises an inner sidewall 542 (only the top edge of which can be seen in the figure) that part-encompasses a driving element that wraps around the pulley 702. This assists in shielding the driving element.

The pulley guards therefore shield the pulleys of the second set of pulleys and the driving elements that wrap around those pulleys. Thus, the pulley guards may advantageously help to prevent unwanted interference with the pulleys and drive elements during operation of the end effector 501.

Furthermore, the pulley guards may assist in the assembly of the end effector. Because the pulley guards part-encompass the drive elements that wrap around the pulleys 701 and 702. The pulleys guards may therefore form a point of alignment used to assist with placing the pulleys 701 and 702 in the correct position during assembly. For example, the curved surface of the interior sidewall can be used to correctly align the pulleys 701 and 702 by placing the pulleys so that they are seated within the channel defined by those surfaces. In effect, the pulley guards may place a further constraint on where the pulleys 701 and 702 may be placed during assembly. This tighter constraint on where the pulleys can be placed can help guide the positioning of the pulleys within the clevis unit.

The pulley arrangement further comprises a pair of redirecting pulleys 716,717. These redirecting pulleys are in the articulation 505 between the first joint 506 and the second and third joints 507, 513. The redirecting pulleys are positioned so as to redirect the second pair of driving elements B1,B2 from the first set of pulleys 601 to the second joint 507 and to redirect the third pair of driving elements C1,C2 from the first set of pulleys 601 to the third joint 513. The redirecting pulleys may be mounted to the supporting body.

The second pair of driving elements B1,B2 is constrained to move around the first redirecting pulley 716. The first redirecting pulley 716 rotates about a first redirecting pulley axis 718. The first redirecting pulley axis 718 is at an angle $\vartheta$ to the first axis 510. The angle $\vartheta$ is such that the first one of the second pair of driving elements B1 is redirected from a take-off point of the first pulley 705 of the first set of pulleys 601 to a pick-up point 721 on the second joint 507. Suitably, the first redirecting pulley 716 comprises a groove which seats the driving element B1. The third pair of driving elements C1,C2 is not constrained to move around the first redirecting pulley 716. However, the second one of the third pair of driving elements C2 does pass by the first redirecting pulley 716 between its take-off point of the third joint 513 and its pick-up point on the first pulley 705 of the first set of pulleys 601. The driving element C2 may be partially enclosed by the first redirecting pulley 716. For example, the driving element C2 may partially pass between the wings of the groove of the first redirecting pulley 716, but the driving element C2 is not seated in the groove of the first redirecting pulley 716.

The third pair of driving elements C1,C2 is constrained to move around the second redirecting pulley 717. The second redirecting pulley 717 rotates about a second redirecting pulley axis 719. The second redirecting pulley axis 719 is at an angle $\psi$ to the first axis 510. The angle $\psi$ is such that the first one of the third pair of driving elements C1 is redirected from a take-off point 720 of the second pulley 706 of the first set of pulleys 601 to a pick-up point on the third joint 513. Suitably, the second redirecting pulley 717 comprises a groove which seats the driving element C1. The second pair of driving elements B1,B2 is not constrained to move around the second redirecting pulley 717. However, the second one of the second pair of driving elements B2 does pass by the second redirecting pulley 717 between its take-off point 720 of the second joint 507 and its pick-up point on the second pulley 706 of the first set of pulleys 601. The driving element B2 may be partially enclosed by the second redirecting pulley 717. For example, the driving element B2 may partially pass between the wings of the groove of the second redirecting pulley 717, but the driving element B2 is not seated in the groove of the second redirecting pulley 717.

A take-off point is the point at which a driving element loses contact with a pulley. A pick-up point is the point at which a driving element first contacts a pulley. For a driving element passing directly from a first pulley to a second pulley, the take-off point of the driving element from the first pulley and the pick-up point of the driving element on the second pulley are points on a line which is tangential to both the first pulley and the second pulley, the take-off point being where that tangential line intersects the first pulley, and the pick-up point being where that tangential line intersects the second pulley. This is for the purposes of explanation only and treats as negligible the thickness of the driving element. Thus, in reality, the tangential line has a thickness equal to the thickness of the driving element, with the take-off point being where one side of the tangential line meets the first pulley, and the pick-up point being where the other side of the tangential line meets the second pulley.

The redirecting pulley 716 causes the driving element B1 to wrap more fully around the second joint 507 than would happen if the redirecting pulley 716 was not there, thereby increasing the length of engagement between the driving element B1 and the second joint 507. Thus, the driving element B1 has a greater travel around the second joint 507, and is hence able to cause a larger rotation of the end effector element 502 about the second axis 512 than would be possible without the redirecting pulley 716. The redirecting pulley 716 causes the pick-up point of the driving element B1 on the second joint 507 to change relative to where it would have been without the redirecting pulley 716.

The redirecting pulley 717 causes the driving element C1 to wrap more fully around the third joint 513 than would happen if the redirecting pulley 717 was not there, thereby increasing the length of engagement between the driving element C1 and the third joint 513. Thus, the driving element C1 has a greater travel around the third joint 513, and is hence able to cause a larger rotation of the end effector element 503 about the second axis 512 than would be possible without the redirecting pulley 717. The redirecting pulley 717 causes the pick-up point of the driving element C1 on the third joint 513 to change relative to where it would have been without the redirecting pulley 717.

The redirecting pulleys are each located towards the outside edge of the articulation, on opposing sides of the articulation. This is more easily seen on FIG. 5a. As seen in FIG. 6a, each redirecting pulley is located between the longitudinal axis of the articulation and the external profile of the articulation, on opposing sides of the articulation. Suitably, the diameter of each redirecting pulley is maximised for the space available. In other words, the redirecting pulley is as large as possible, whilst enabling one driving element to engage the pulley on one side of the pulley and another driving element to pass next to the pulley on the opposing side of the pulley without snagging, the pulley and the two driving elements being encapsulated within the profile of the articulation.

The first redirecting pulley 716 is located in a plane defined by the following three points: (i) the desired take-off point of driving element B1 from the first pulley 705 of the first set of pulleys 601, (ii) the desired pick-up point of driving element B1 on the second joint 507, and (iii) a point on the boundary of the articulation, the point being such that the first redirecting pulley 716 is encapsulated within the boundary of the articulation when located in the plane. Suitably, the first redirecting pulley 716 is as large as possible whilst still being located in this plane, encapsulated within the profile of the articulation, not impeding the path of the driving element C2, and enabling driving element B1 to freely move around it.

The second redirecting pulley 717 is located in a plane defined by the following three points: (i) the desired take-off point of driving element C1 from the second pulley 706 of the first set of pulleys 601, (ii) the desired pick-up point of driving element C1 on the third joint 513, and (iii) a point on the boundary of the articulation, the point being such that the second redirecting pulley 717 is encapsulated within the boundary of the articulation when located in the plane. Suitably, the second redirecting pulley 717 is as large as possible whilst still being located in this plane, encapsulated within the profile of the articulation, not impeding the path of the driving element B2, and enabling driving element C1 to freely move around it.

The desired take-off points and pick-up points are determined so as to allow the desired travel of the driving elements around the second and third joints so as to allow the desired maximum rotation of the end effector elements about the second axis.

The first and second redirecting pulleys are located in different planes. As can be seen in FIG. 6a, those planes may be symmetrical about a plane which is perpendicular to the first axis 510. Those planes may be rotationally symmetrical about a plane which is perpendicular to the first axis 510. Specifically, those planes may be rotationally symmetrical about a line in a plane which is perpendicular to the first axis 510. When the instrument is in the straight configuration illustrated in FIG. 6a, those planes are rotationally symmetrical about the longitudinal axis of the shaft 511. This is second order rotational symmetry. Those planes may be a reflection of each other in the plane which is perpendicular to the first axis 510. In the example illustrated, the end effector elements 502 and 503 are rotationally symmetrical, and the paths of the driving elements about the joints 507 and 513 are rotationally symmetrical. Alternatively, the axes of the end effector elements 502 and 503 may be rotationally asymmetrical and/or the paths of the driving elements about the joints 507 and 513 may be asymmetrical. The paths of the driving elements about the joints 507 and 513 may be asymmetrical as a result of the joints having different diameters (to enable different tension ratios) and/or being positioned at different offsets from the centreline of the supporting body 509. In any of these alternative examples, the first and second redirecting pulleys 716 and 717 would not be rotationally symmetric. They would have different sizes and/or different positions in order to cause the driving elements to have the desired take-off points and pick-up points as previously described.

Suitably, the whole pulley arrangement comprising the first set of pulleys, the second set of pulleys and the redirecting pulleys is symmetrical about a plane which is perpendicular to the first axis 510. Specifically, a first partial arrangement comprising the first pulley of the first set of pulleys 705, the first pulley of the second set of pulleys 701, and the first redirecting pulley 716 is rotationally symmetrical to a second partial arrangement comprising the second pulley of the first set of pulleys 706, the second pulley of the second set of pulleys 702, and the second redirecting pulley 717 about a plane which is perpendicular to the first axis 510. Suitably, the first partial arrangement is a reflection of the second partial arrangement in the mentioned plane which is perpendicular to the first axis 510. The second pair of driving elements B1,B2 is constrained to move around the pulley arrangement in a rotationally symmetrically opposing manner to that in which the third pair of driving elements C1,C2 is constrained to move around the pulley arrangement. Since the pulley arrangement has the described symmetry, the second and third driving elements that are constrained to move symmetrically around the pulley arrangement also have the same symmetry. Thus, the path of the second pair of driving elements B1,B2 about the pulley arrangement is rotationally symmetrical to the path of the third pair of driving elements C1,C2 about the pulley arrangement.

The above examples described a clevis unit having a pulley arrangement and two pulley guards. It will be appreciated that in an alternative arrangement, the clevis unit may include only a single pulley guard. Furthermore, the pulley guards may be implemented within an end effector that comprises a different pulley arrangement to the arrangement described herein. Such an arrangement may not include the redirecting pulleys, for example. In another example variation, the pulleys of the pulley arrangement may not be formed of two pulley elements, but may be formed of a single pulley element. The pulley arrangement may have additional pulleys not included in the examples described herein.

In the examples described herein instrument articulation included three joints. It will be appreciated that in other examples the articulation may contain a greater or fewer number of joints. For example, in an alternative example the end effector may only have one end effector element. In this case, the articulation may not include the third joint 513, or the associated pulleys and drive elements to drive that joint.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:
1. A surgical robotic instrument comprising:
a shaft;
an end effector element;
an articulation connecting the end effector element to the shaft, the articulation comprising:
a first joint driveable by a first pair of driving elements, the first joint permitting the end effector element to rotate about a first axis transverse to a longitudinal axis of the shaft;
a second joint driveable by a second pair of driving elements;

a pulley arrangement around which the second pair of driving elements is constrained to move, the pulley arrangement comprising:
  a first set of pulleys rotatable about the first axis; and
  a second set of pulleys proximal to the first set of pulleys and comprising a first pulley rotatable about a second axis, and a second pulley rotatable about a third axis parallel to and offset from the second axis; and
a clevis unit comprising two arms supporting the first set of pulleys and the second set of pulleys of the pulley arrangement, and a pulley guard extending from one of the arms configured to guard one of the first and second pulleys.

2. A surgical robotic instrument as claimed in claim 1, wherein the second joint is distal to the first joint.

3. A surgical robotic instrument as claimed in claim 1, wherein the second and third axes are offset from the first axis.

4. A surgical robotic instrument as claimed in claim 3, wherein the second and third axes are offset from the first axis in a direction transverse to the longitudinal axis of the shaft.

5. A surgical robotic instrument as claimed in claim 3, wherein the second and third axes lie in a plane perpendicular to the longitudinal axis of the shaft.

6. A surgical robotic instrument as claimed in claim 1, wherein the first axis intersects the longitudinal axis of the shaft.

7. A surgical robotic instrument as claimed in claim 1, wherein the second and third axes are parallel to the first axis.

8. A surgical robotic instrument as claimed in claim 1, wherein a first of the two arms supports the first pulley, and a second of the two arms supports the second pulley.

9. A surgical robotic instrument as claimed in claim 1, wherein the first and second arms are on opposing sides of a plane that contains the longitudinal axis of the shaft and is transverse to the first axis.

10. A surgical robotic instrument as claimed in claim 1, wherein the clevis unit comprises a first pulley guard extending from the first arm configured to guard the first pulley, and a second pulley guard extending from the second arm configured to guard the second pulley.

11. A surgical robotic instrument as claimed in claim 10, wherein the first and second pulley guards are located on opposing sides of a first plane that contains the longitudinal axis of the shaft, and is transverse to the first axis, and on opposing sides of a second plane that contains both the longitudinal axis of the shaft and the first axis.

12. A surgical robotic instrument as claimed in claim 10, wherein the clevis unit further comprises first and second drive element guides, one driving element of the first pair of driving elements passing through the first drive element guide, and the other driving element of the first pair of driving elements passing through the second element guide, each of the first and second drive element being located between the first and second arms of the clevis unit.

13. A surgical robotic instrument as claimed in claim 10, wherein the first pulley guard comprises an interior sidewall that part-encompasses the first pulley, and the second pulley guard comprises an interior sidewall that part-encompasses the second pulley.

14. A surgical robotic instrument as claimed in claim 1, wherein the pulley guard is located within an interior space of the clevis unit bound by the profile of the shaft.

15. A surgical robotic instrument as claimed in claim 1, wherein the clevis unit further comprises first and second drive element guides, one driving element of the first pair of driving elements passing through the first drive element guide, and the other driving element of the first pair of driving elements passing through the second drive element guide, each of the first and second drive element guides being located between the first and second arms of the clevis unit.

16. A surgical robotic instrument as claimed in claim 15, wherein the pulley guard extends between said one of the arms and one of the drive element guides.

17. A surgical robotic instrument as claimed in claim 15, wherein the clevis unit comprises a first pulley guard extending from the first arm configured to guard the first pulley, and a second pulley guard extending from the second arm configured to guard the second pulley, wherein the first pulley guard extends between the first arm and first drive element guide, and the second pulley guard extends between the second arm and second drive element guide.

18. A surgical robotic instrument as claimed in claim 15, wherein the first and second driving element guides are located on opposing sides of a plane containing the longitudinal axis of the shaft and the first axis.

* * * * *